United States Patent [19]

Semler et al.

[11] Patent Number: 5,017,291

[45] Date of Patent: May 21, 1991

[54] PROCESS FOR RECYCLING AND RECONSTITUTING FLEXOGRAPHIC INKS

[75] Inventors: Loren H. Semler, Lake Forest; Joseph M. Palm, Lombard; Paul B. Englram, Carol Stream; Jon Y. Clegg, Elmhurst, all of Ill.

[73] Assignee: Semler Industries, Inc., Franklin Park, Ill.

[21] Appl. No.: 605,190

[22] Filed: Oct. 24, 1990

[51] Int. Cl.$^5$ .............................................. B01D 61/58
[52] U.S. Cl. ..................... 210/641; 210/641; 210/650; 210/651; 210/652; 101/366
[58] Field of Search ............... 210/641, 649, 650, 651, 210/652; 101/366, 364; 134/10

[56] References Cited

U.S. PATENT DOCUMENTS

| | | | |
|---|---|---|---|
| 3,896,730 | 7/1975 | Garrett et al. | 101/425 |
| 4,000,065 | 12/1976 | Ladha et al. | 210/652 |
| 4,165,288 | 8/1979 | Teed et al. | 210/652 |
| 4,391,638 | 7/1983 | Fusco et al. | 210/805 |
| 4,563,638 | 1/1986 | Zucker | 210/774 |
| 4,808,237 | 2/1989 | McCormick et al. | 101/425 |
| 4,818,284 | 4/1989 | McKelvey | 210/787 |

FOREIGN PATENT DOCUMENTS 8805444  7/1988  Sweden ............................. 210/652

OTHER PUBLICATIONS

Reduction of Fluorine Waste and Reclamation of Water (IBM Tech. Discl. Bul., vol. 19, No. 8, Jan. 1977, pp. 3016-3017.

Primary Examiner—W. Gary Jones
Assistant Examiner—Abeer Daoud
Attorney, Agent, or Firm—Tilton, Fallon, Lungmus

[57] ABSTRACT

A process for recycling and reconstituting flexographic inks from wash water resulting from cleaning the rollers and other components of a flexographic printing press. The process includes the steps of circulating the wash water through a cross-flow ultrafilter to separate an optically-clear filtrate from a first concentrate containing suspended ink solids, bacteria, and macromolecules. Thereafter, the filtrate is directed through a reverse-osmosis filter to separate from the filtrate a second concentrate containing dissolved ink components and the remaining bacteria. The first and second concentrates are then combined together with a compatible biocidal agent to form a stable, biologically-inactive additive that is mixed with fresh ink concentrate to form press-ready flexographic printing ink.

6 Claims, 2 Drawing Sheets

PROCESS FOR RECYCLING AND RECONSTITUTING FLEXOGRAPHIC INKS

BACKGROUND AND SUMMARY

This invention is particularly concerned with the disposition of water-based inks washed from high-speed presses commonly known as flexographic printing presses. While flexographic technology may also have limited applicability in printing operations that use other types of inks, the use of such technology with water-based inks is so predominant that flexography is generally considered synonymous with high-speed printing using water-based inks.

Since water-based inks dry by evaporation, such inks tend to clog the analox rollers and other parts of a flexographic press unless the ink is washed away by water following a printing operation. The problem, which has become increasingly severe because of environmental concerns, is how to dispose of the ink-laden wash water.

In general the disposal procedure has involved treating the water to concentrate and dry the solids so they can be discarded as solid waste. Several concentration techniques have been developed, some of which are elaborate and none of which is entirely satisfactory. One approach involves adding chemicals to precipitate the ink components. The precipitate is then dried and discarded. Another involves the use of a rotary-drum vacuum filter which similarly separates out the ink components which are then dried and discarded. Still another involves biological digestion of the ink. Ultrafiltration has also been used.

While some efforts have been made to use recycled wash water for purposes of cleaning presses and also for diluting fresh ink concentate in makeready operations, such efforts have been notably unsuccessful. See, for example, MacAdam et al, "How the Miami Herald Overcame Problems in Newsflexo Printing," FLEXO, pages 30-38, June 19 1989. Agents used to coagulate the solid residue in wash water so that it may then be precipitated out as a relatively coarse sludge, leaving a clear water effluent, were found also to introduce ions into the decanted liquid that would erupt printing operations when the clear water was used to prepare fresh batches of flexographic ink. Even if such a procedure could have been performed successfully, the only component of the wash water subject to recycling would have been the decanted water; the precipitated ink sludge would have still required waste disposal.

Accordingly, a main aspect of this invention lies in providing a process for treating wash water from the cleaning of flexographic rollers and presses so that the ink residue may be effectively recycled for use in reformulating flexographic ink and, if desired, the optically-clear water filtrate may also be recycled for use as wash water in cleaning the rollers and presses. The process therefore allows all constituents of wash water to be recycled for use in pressroom operations.

More particuarly, the invention lies in part in recognizing that a concentrate obtained from wash water may serve as a suitable additive in making up ink for use by flexographic presses if that concentrate has substantially the same solids and ionic content as fresh ink. An additive having such qualities may be obtained pursuant to this discovery if the wash water from a flexographic press is first passed through an ultrafilter and if the filtrate or permeate is then directed through a reverse-osmosis membrane filter, and if the concentrates from both stages of filtration are then mixed with each other and with a biocidal agent. Such a mixed concentrate has been found so close to fresh ink forumlation, except for viscosity (which is controlled by the volume of water added to the ink), that even ink manufacturers have detected virtually no discernible differences between ink prepared using only fresh ingredients and ink prepared by mixing fresh ingredients with the treated concentrate or residue.

Briefly, the process involves circulating wash water obtained from washing the rollers, fountains, and associated parts of a flexographic press through an ultrafilter, preferably a cross-flow ultrafilter, to separate an optically-clear filtrate or permeate from a flowable first concentrate containing suspended ink solids and macromolecules having molecular weights greater than 20,000. The term "optically clear" as used here means that the filtrate or permeate is free of suspended solids and, although possibly tinted and not completely colorless, is nevertheless transparent.

In the second stage of the batch processing, the optically-clear filtrate is directed through a reverse-osmosis filter to separate from that filtrate a flowable second concentrate containing dissolved ink components. Since the reverse-osmosis filter blocks the passage of bacteria not already separated out by the first stage, the filtrate resulting from the second stage is not only optically-clear, and now substantially colorless, but also bacteria-free. Virtually all bacteria that existed in the wash water is retained in the first and second concentrates. The first and second concentrates from the two stages are then mixed together and a compatible biocidal agent is added to produce a stable, biologically-inactive additive suitable for mixing with fresh ink concentrate to form printing ink.

The clear filtrate from which the dissolved ink components and bacteria have been removed may be recycled as wash water for further cleaning operations. While such water meets or exceeds known standards, for industrial discharge, the process preferably includes a further stage in which such water is directed through an activated carbon filter so that the resulting water then meets the highest quality standards so far established.

Other features, objects, and advantages of the invention will become apparent from the specification and drawings.

DRAWINGS

DETAILED DESCRIPTION OF PREFERRED EMBODIMENT

Figure 1:
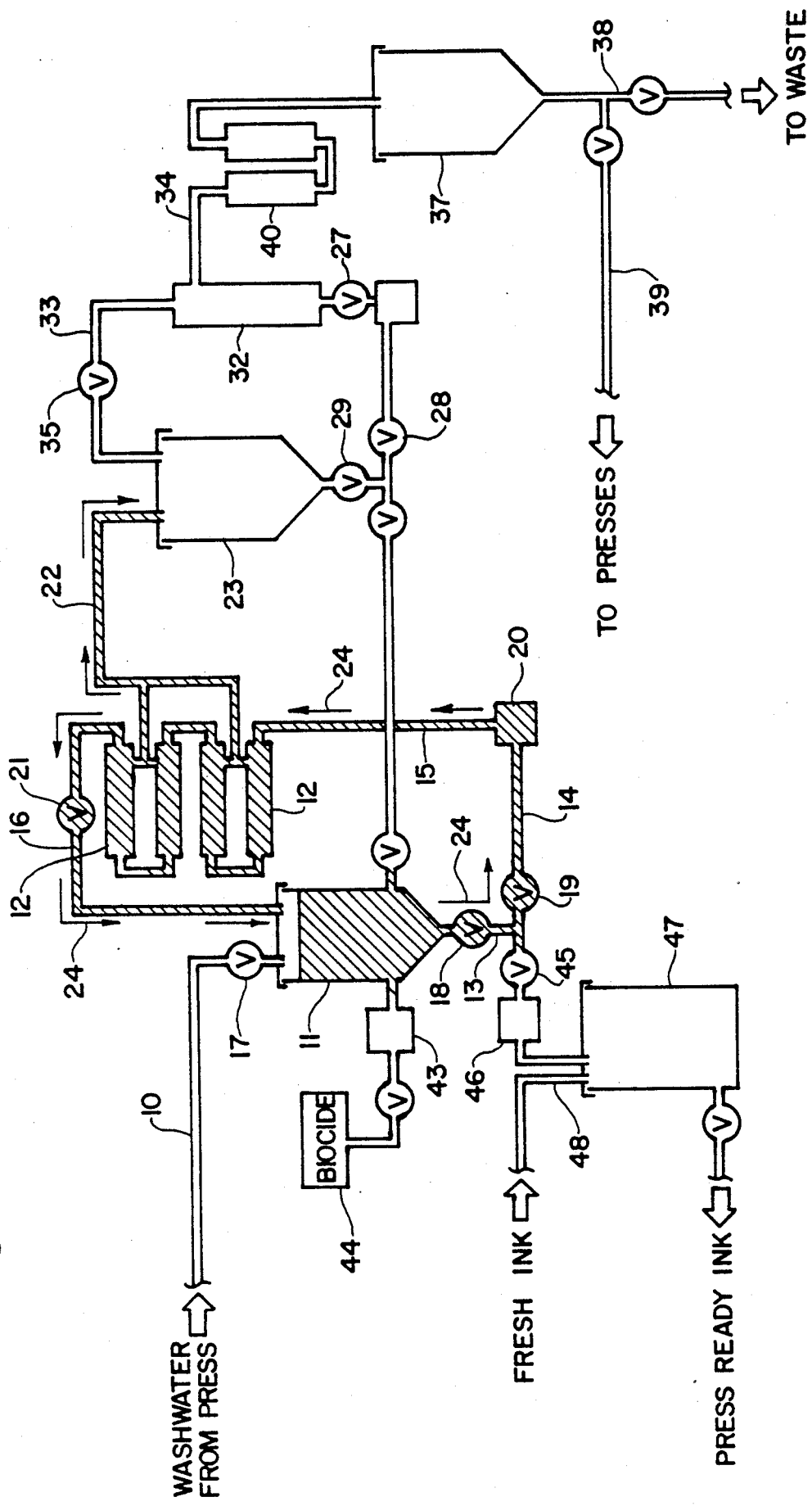
FIG. 1 is a schematic view of a flexographic wash water recovery system during a first stage of operation.

Referring to the drawings, wash water from the cleaning of flexographic rollers and presses is directed through line 10 into receiving tank 11. The tank communicates with a cross-flow ultrafilter 12 through outflow conduits 13, 14, and 15, and a return conduit 16 extends from the ultrafilter 12 back to tank 11. Valves 17, 18, and 19 control the circulation of flow from the tank through the ultrafilter and back to the tank. Pump 20 directs the fluid circulation and throttling valve 21 downstream from the ultrafilter 12 restricts the flow through line 16 and thereby creates a back pressure within the ultrafiltration modules. Such pressurization causes optically-clear filtrate or permeate to pass through the membranes of the ultrafiltration modules into conduit 22 leading to a second tank 23.

Any of a variety of commercially-available ultra-filtration systems may be used as long as they are capable of blocking the passage of all particulates, suspended solids, and macromolecules. In this context, a macromolecule is regarded as one that has a molecular weight in excess of 20,000. Effective results have been obtained using an ultrafilter element of the cross-flow type, that is, with the direction of fluid flow being parallel with the filtration membrane, marketed by Nitto, Santa Clara, Calif., under the designation NTU-2020-M7. It is believed that other commercially-available ultra-filtration elements, such as those marketed by Koch Membrane Systems, Wilmington, Mass. may also be used.

Figure 2:
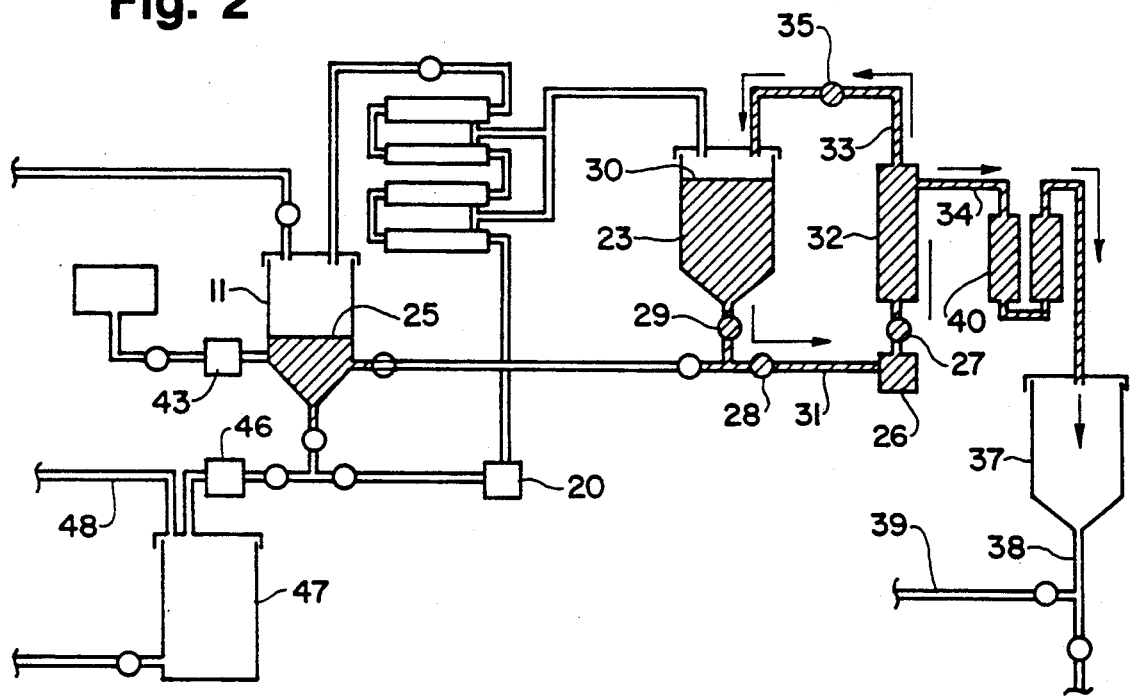
FIG. 2 is a schematic view similar to FIG. 1 but showing the system in a second stage of operation.

Tank 11 has sensors (not shown) at different elevations so that pump 20 is automatically activated, and valve 17 automatically closed, when the tank is filled to a selected level with wash water. The wash water is circulated as indicated by arrows 24 in FIG. 1 with the ink-laden wash water in tank 11 becoming more concentrated, and reducing in volume, as optically-clear water is extracted by the ultra-filtration system and is discharged into tank 23. FIG. 2 depicts the system at the end of the ultra-filtration stage where the level of fluid in tank 11 has reached a shut-off point and operation of pump 20 has been automatically interrupted. What remains in tank 11 is a flowable first concentrate 25 containing suspended ink solids and macromolecules. The dissolved ink components have generally passed into tank 23 with the optically-clear filtrate.

Upon activation of pump 26, with valves 27, 28 and 29 in open condition, the filtrate solution 30 in tank 23 is pumped from the tank through line 31 through a reverse-osmosis membrane filter 32. The filter separates the flow into two fractions, one being a concentrate that is returned to tank 23 through line 33 and the other being the filtrate or permeate that passes through the membrane and is carried from the reverse-osmosis filter by means of line or conduit 34 (FIG. 2).

The pump 26 may be automatically activated when the level of fluid 30 in tank 23 reaches a predetermined level that is mechanically or electronically sensed by any conventional sensing means (not shown). The circulation system is pressurized by a throttling valve 35 in line 33 which, as is well known in the art pertaining to reverse osmosis systems, is adjusted to create a back pressure exceeding osmotic pressure, thereby causing the selective migration of water molecules through the membrane into line 34. The solute molecules remain behind and are circulated back to tank 23 through line 33. Also, since the membrane blocks the passage of bacteria, those microorganisms in the system that have not already been removed in the first stage are blocked by membrane filter 32 and are returned to tank 23. The filtrate passing into conduit 34 is therefore substantially pure, clear, bacteria-free water meeting or exceeding established standards for industrial discharge.

The term "reverse-osmosis" is here used to designate generically those filters which operate on osmotic principles and in which flow is reversed because of pressurization in excess of osmotic pressure. As such, the term includes conventional nanofilters, which by definition involve separation of molecular components having molecular weights ranging between 200 to 2500, as well as true reverse-osmosis filters capable of separating components having molecular weights as low as 50. As a practical matter, it has been found that a filter having a finite molecular cutoff of 250 or less may be used effectively in this system. Such a filter results in the separation of the ionic components of ink as well as all of the bacteria from the filtrate passing into line 34.

Figure 3:
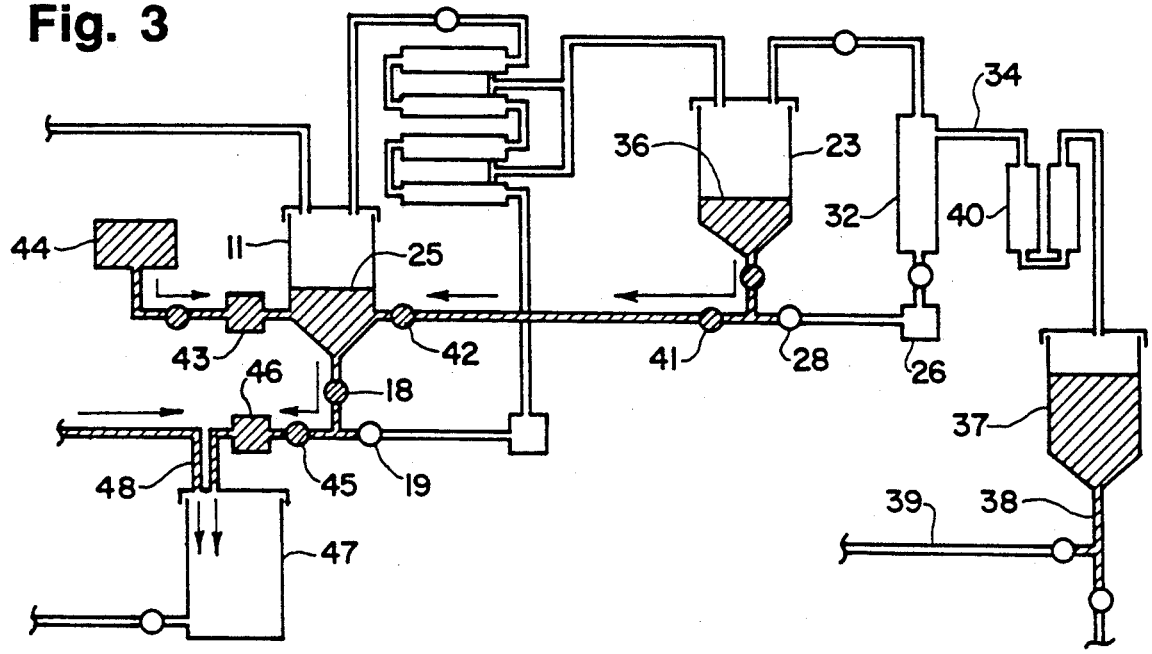
FIG. 3 is a similar schematic view depicting the system in a final operating stage.

As pump 26 continues to operate, the solution returned to tank 23 becomes increasingly concentrated in dissolved ink components. Also, as pure water is separated from the system, passing through the filter into line 34, the volume of fluid in tank 23 progressively diminishes. When the level in tank 23 has dropped to a predetermined level, pump operation is manually or automatically interrupted, leaving a second concentrate 36 in tank 23, the term "second" being used to distinguish it from the first concentrate 25 remaining in tank 11 (FIG. 3).

It is believed that any of a number of standard, commercially-available reverse-osmosis filters may be used as filter 32 in this system. As indicated, the filter should have a molecular weight cutoff of 250 or less. Effective results have been achieved utilizing a reverse-osmosis membrane filter Model 729-S4 supplied by Nitto, Santa Clara, Calif., but other reverse-osmosis filters, or nanofilters, having similar capabilities, such as those marketed by FilmTec Corporation, Minneapolis, Minn., may be used.

The pure water discharge line 34 may connect with the municipal waste systems or with a storage tank 37 which in turn may selectively discharge through line 38 into waste systems or instead communicate with discharge line 39 leading back to the pressroom. In the system depicted in drawings, either option may be selected. Ideally, the water in tank 37 is routed back to the pressroom where it may be used for washing flexographic rollers and associated equipment.

It is also preferred that one or more carbon filters 40 be interposed along line 34 between reverse-osmosis filter 32 and tank 37. While the water discharged from filter 32 meets established purity standards for industrial discharge, the inclusion of activated carbon filters 40 insures that trace impurities will be adsorbed and that the filtrate will meet the highest or strictest standards of purity for industrial discharge. While any of a number of commercially-available activated carbon filters might be used, the effective results have been achieved using grannular carbon filters, 60 percent active and 12 by 30 mesh size, obtained from Sutcliffe, Lutherville, Md.

With the system in the condition depicted in FIG. 3, the first concentrate 25 is retained in tank 11 and the second concentrate 36 in tank 23. Valve 28 is closed and and valves 29, 41, and 42 are opened so that the fluid concentrate 36 in tank 23 will drain into tank 11. The combined concentrates in tank 11 contain in diluted form the same constituents as the original printing ink without any additives having been introduced by the system. The combined concentrates also include bacteria which, if given sufficient time, may degrade or alter the ink residue and also produce byproducts that may be objectionable because of odor or other reasons. Therefore, following the combining of the concentrates in tank 11, valve 42 is closed and pump 43 is activated to introduce a suitable biocidal agent from reservoir 44 into tank 11. Thereafter, valves 18 and 45 are opened, valve 19 is closed, and pump 46 is activated to pump the concentrate-biocide mixture into mixing reservoir 47. The mixture pumped from tank 11 is in the form of a stable, fluidic biologically-inactive additive suitable for mixing directly with fresh ink concentrate to form pressready printing ink. The addition of fresh ink concentrate is diagramatically depicted in FIG. 3, such concentrate being introduced into reservoir 37 through conduit 48. It will be understood that the viscosity of the fresh ink concentrate would be controlled so that when the fresh ink is combined with the additive, the resulting pressready printing ink be of the desired final viscosity.

Any biocidal agent may be used that is effective in destroying bacteria and has no adverse effects on the ink, the printing equipment, or their performance. Effective results have been obtained using a biocide commercially available as Troysan 186 from Troy Chemical, Newark, N.J., but other suitable biocidal agents of the type commonly used in the formulation of water-based paints and adhesives may be used.

It is believed apparent from the above that the system is, in effect, a closed-circuit system for ink components since all of the ink constituents, both particulate and ionic, obtained from the wash water are recycled to the presses for use as ink. The only constituent that is not necessarily recycled is the bacteria-free, optically-clear water collected in tank 37, and even that constituent may be recycled by using it as wash water for subsequently cleaning the printing rollers and presses.

While in the foregoing we have disclosed an embodiment of the invention in considerable detail for purposes of illustration, it will be understood by those skilled in the art that many of these details may be varied without departing from the spirit and scope of the invention.

We claim:

1. A process for recycling water-based printing inks comprising the steps of circulating wash water obtained from washing the rollers of a flexographic press through an ultrafilter to separate an optically-clear filtrate and a fluid first concentrate containing suspended ink solids; directing said optically-clear filtrate through a reverse-osmosis filter to separate from said filtrate a fluid second concentrate containing dissolved ink components and bacteria; combining said first and second concentrates with a compatible biocidal agent to form a stable, biologically-inactive additive suitable for mixing with fresh ink concentrate to form pressready printing ink.

2. The process of claim 1 in which there is the further step of using said optically-clear filtrate, from which dissolved ink components and bacteria have been removed by said reverse-osmosis filter, to wash printing rollers of a flexographic press; and thereafter subjecting said filtrate so used as wash water to the process steps of claim 1.

3. The process of claim 1 in which there is the further step of directing said filtrate from said reverse-osmosis filter through an activated carbon adsorption filter.

4. The process of claim 1 in which said circulating step comprises separating from said wash water suspended ink solids and macromolecules having molecular weights of 20,000 and more.

5. The process of claims 1 or 4 in which said wash water is placed in a first tank and said circulating step comprises continuously circulating the contents of said tank through said ultrafilter until enough optically-clear filtrate has been separated to reduce the contents of said first tank to a predetermined volume.

6. The process of claim 1 in which there is the further step of mixing said additive with fresh ink concentrate to form pressready printing ink of selected viscosity.

* * * * *